United States Patent
Mulders et al.

(10) Patent No.: US 9,206,504 B2
(45) Date of Patent: Dec. 8, 2015

(54) LOW ENERGY ION MILLING OR DEPOSITION

(71) Applicant: FEI Company, Hillsboro, OR (US)

(72) Inventors: Johannes Jacobus Lambertus Mulders, Eindhoven (NL); Remco Theodorus Johannes Petrus Geurts, Oss (NL); Petrus Hubertus Franciscus Trompenaars, Tilburg (NL); Eric Gerardus Theodoor Bosch, Eindhoven (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/243,583

(22) Filed: Apr. 2, 2014

(65) Prior Publication Data

US 2014/0302252 A1    Oct. 9, 2014

(30) Foreign Application Priority Data

Apr. 3, 2013   (EP) .................................. 13162084

(51) Int. Cl.
*C23C 14/28* (2006.01)
*H05B 6/00* (2006.01)
(Continued)

(52) U.S. Cl.
CPC ................. *C23C 14/48* (2013.01); *G01N 1/286* (2013.01); *G01N 1/32* (2013.01); *H01J 37/02* (2013.01);
(Continued)

(58) Field of Classification Search
CPC ...... C23C 14/48; H01J 37/31; H01J 37/3178; H01J 37/3053; H01J 37/026; H01J 31/3056
See application file for complete search history.

(56) References Cited

U.S. PATENT DOCUMENTS 5,055,696 A * 10/1991 Haraichi et al. ........... 250/492.2
5,958,799 A *  9/1999 Russell et al. ............. 438/712
(Continued)

FOREIGN PATENT DOCUMENTS

EP     1491654      12/2004
EP     1821146       8/2007
(Continued)

OTHER PUBLICATIONS

Unknown, "Improving High Resolution TEM Images using Low Energy Ion Milling," South Bay Technology, Inc. Applications Laboratory Report 68, www.southbaytech.com/appnotes/68%20Improving%20High%20Resolution%20TEM%20Images%20using%20Low%20Energy%20Ion%20Milling.pdf,pp. 1-4, Sep. 2002.

(Continued)

*Primary Examiner* — Michael Wieczorek
(74) *Attorney, Agent, or Firm* — Scheinberg & Associates, PC; Michael O. Scheinberg; John E. Hillert

(57) ABSTRACT

Samples to be imaged in a Transmission Electron Microscope must be thinned to form a lamella with a thickness of, for example, 20 nm. This is commonly done by sputtering with ions in a charged particle apparatus equipped with a Scanning Electron Microscope (SEM) column, a Focused Ion Beam (FIB) column, and one or more Gas Injection Systems (GISses). A problem that occurs is that a large part of the lamella becomes amorphous due to bombardment by ions, and that ions get implanted in the sample. The invention provides a solution by applying a voltage difference between the capillary of the GIS and the sample, and directing a beam of ions or electrons to the jet of gas. The beam ionizes gas that is accelerated to the sample, where (when using a low voltage between sample and GIS) low energy milling occurs, and thus little sample thickness becomes amorphous.

14 Claims, 3 Drawing Sheets

Figure 1:
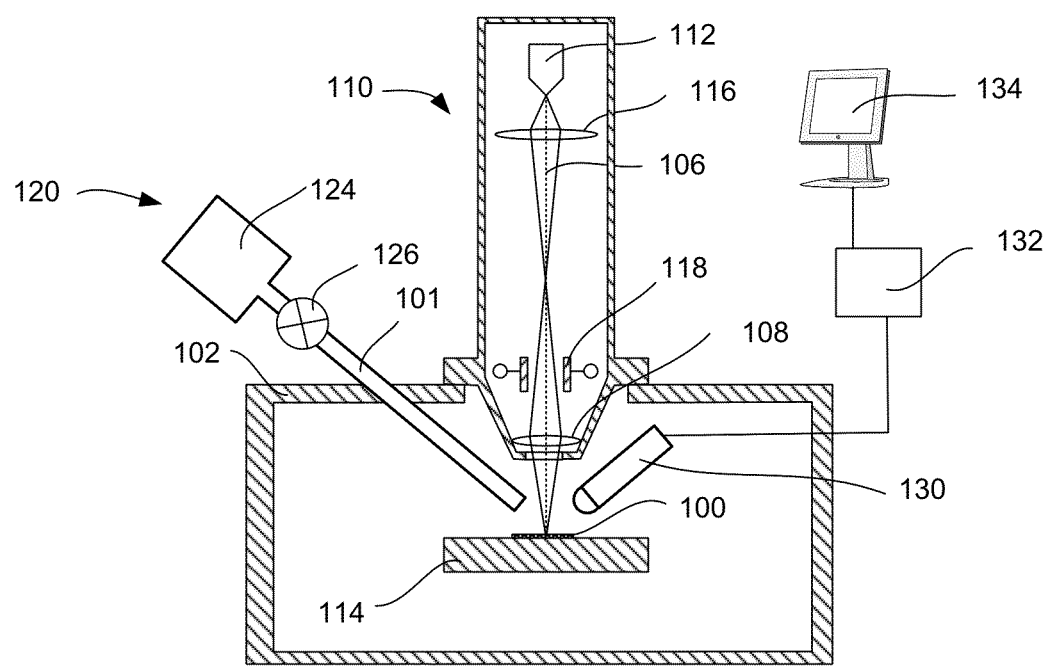

(51) Int. Cl.
*C23C 14/48* (2006.01)
*H01J 37/305* (2006.01)
*H01J 37/317* (2006.01)
*H01J 37/02* (2006.01)
*G01N 1/28* (2006.01)
*G01N 1/32* (2006.01)

(52) U.S. Cl.
CPC ......... *H01J 37/3053* (2013.01); *H01J 37/3171* (2013.01); *H01J 37/3178* (2013.01); *H01J 2237/004* (2013.01); *H01J 2237/006* (2013.01); *H01J 2237/3174* (2013.01); *H01J 2237/31732* (2013.01); *H01J 2237/31742* (2013.01); *H01J 2237/31745* (2013.01); *H01J 2237/31749* (2013.01)

(56) References Cited

U.S. PATENT DOCUMENTS

| | | |
|---|---|---|
| 6,211,527 B1 | 4/2001 | Chandler |
| 6,268,608 B1 | 7/2001 | Chandler |
| 7,150,811 B2 | 12/2006 | Miller |
| 7,205,237 B2 * | 4/2007 | Deering et al. ............... 438/690 |
| 7,670,956 B2 | 3/2010 | Bret et al. |
| 7,675,049 B2 * | 3/2010 | Schmidt et al. .......... 250/492.21 |
| 8,617,668 B2 | 12/2013 | Toth et al. |
| 2010/0197142 A1 | 8/2010 | Randolph et al. |
| 2011/0204263 A1 * | 8/2011 | Phaneuf et al. ............ 250/492.2 |
| 2012/0003394 A1 | 1/2012 | Mulders et al. |
| 2012/0308740 A1 | 12/2012 | Randolph et al. |
| 2013/0068611 A1 | 3/2013 | Botman et al. |
| 2013/0248356 A1 | 9/2013 | Rue |

FOREIGN PATENT DOCUMENTS

| | | |
|---|---|---|
| JP | 2008-098232 | 4/2008 |
| JP | 2011-243997 | 12/2011 |
| WO | 97/49116 | 12/1997 |

OTHER PUBLICATIONS

Unknown, "Using Beam Chemistries with SEM, FIB and DualBeam(TM) for Surface Modification", www.fei.com/uploadedfiles/documents/content/an-gis_beam_chemistries-an-web-2010.pdf, pp. 1-8, Apr. 2010.

* cited by examiner

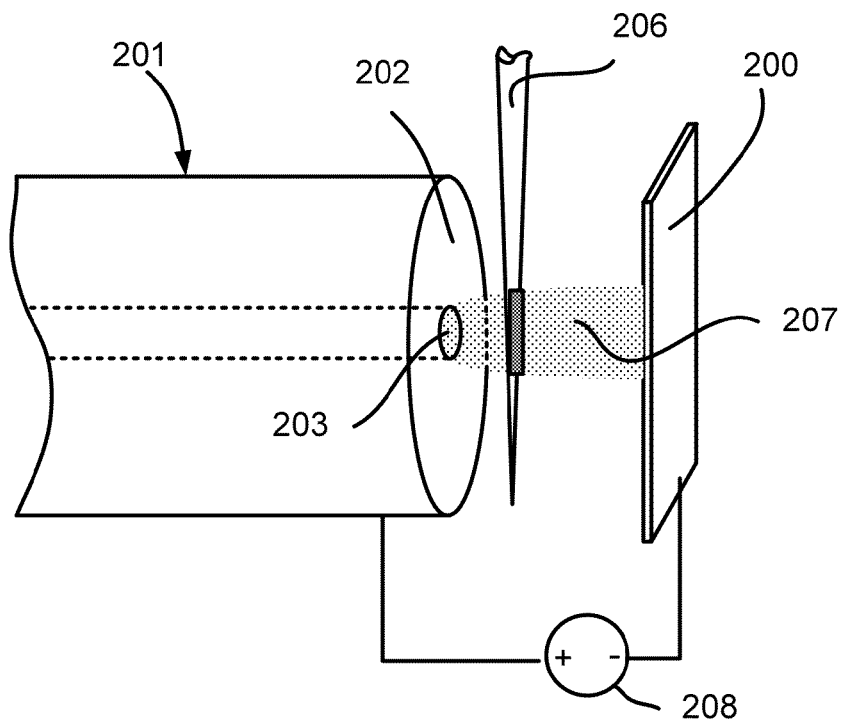
FIG. 2
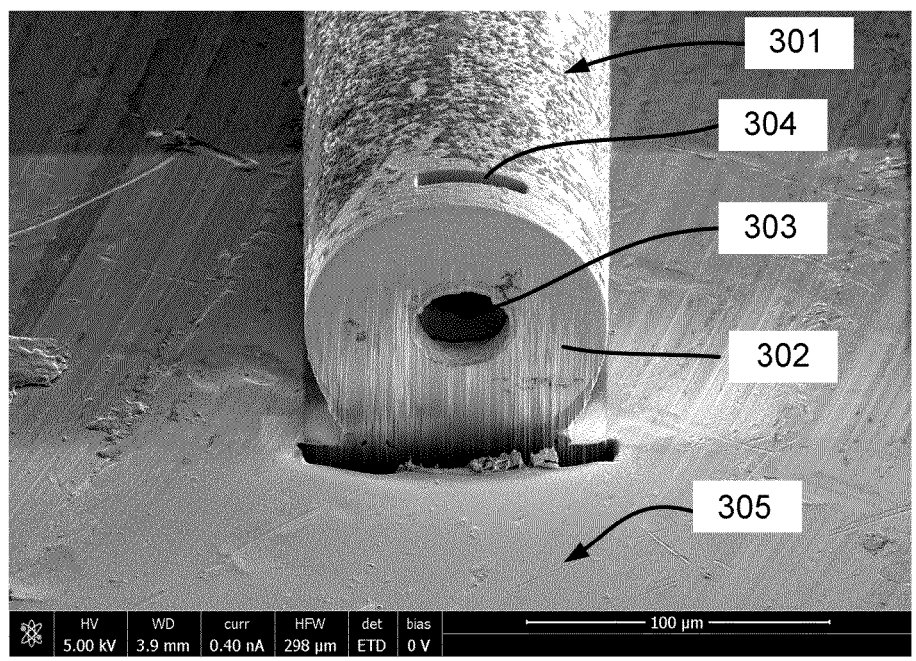
FIG. 3ᵃ

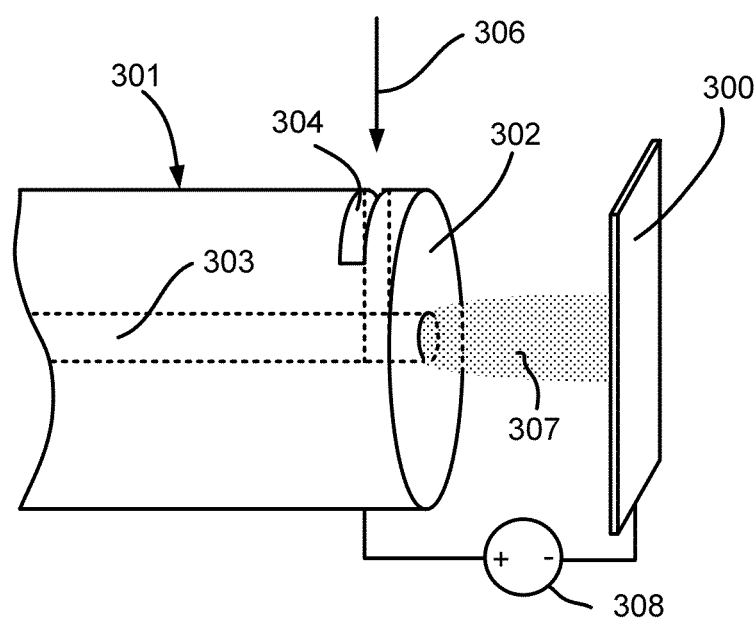
FIG. 3$^b$ ns from the gas injection system. These secondary ions are then accelerated to the sample. The secondary ions are generated between the gas injection system and the sample. As the ions are formed between electrode and sample, the energy with which they impinge on the sample is at most the voltage difference between sample and electrode. Therefore it is possible to produce a beam of secondary ions that is proportional to the beam of primary charged particles (electrons or ions), and, assuming a voltage difference U between electrode and sample the energy with which they hit the sample is between zero and U eV.

LOW ENERGY ION MILLING OR DEPOSITION

The invention relates to a method for removing material from a work piece or depositing material on a work piece using a charged particle apparatus, the charged particle apparatus equipped with:

- a column for producing a beam of charged particles mounted on an evacuable sample chamber,
- a sample position located in the sample chamber, and
- a gas injection system for directing a jet of gas to the sample position, the method comprising
- providing a work piece at the sample position,
- evacuating the sample chamber, and
- directing a jet of gas emerging from a gas injection system to the work piece.

This method is used, for example, for thinning a work piece (a sample), for example a semiconductor sample, for further inspection with a Transmission Electron Microscope (TEM) or a Scanning Electron Microscope (SEM). Samples thinned with the prior art method have a thickness down to 25 nm or less.

This method, known to the skilled person as "Focused Ion Beam milling" or "FIB milling", further includes directing the charged particle beam, typically a beam of energetic ions with an energy of between, for example, 1 keV to 40 keV, to the work piece. As a result local etching and/or deposition occurs due to the impacting ions and the adsorbed gas. For etching an etchant, for example $XeF_2$ or $H_2O$, is directed to the sample, while for deposition a precursor, such as $MeCpPtMe_3$ (used for Pt deposition), $W(CO)_6$ (used for tungsten deposition) and naphthalene (used for carbon deposition), is directed to the sample. See also Application Note AN0024 03-2010 of FEI Company, Hillsboro, USA.

A problem occurs in that when thinning a sample, such as a semiconductor sample, part of the surface of the sample becomes amorphous due to the bombardment with the energetic ions. Typically the amorphous layer is thicker when the energy of the ions is higher. Therefore the ion energy used is comparatively low, for example 1 keV or less. In most commonly used samples such as steel and silicon based samples, the typical damage layer is in the range of 2-5 nm.

It is noted that the ion beam is often produced by a so-named Liquid Metal Ion Source (LMIS), the most popular LMIS producing gallium ions. A related problem is the implantation of the energetic ions, for example gallium, into the sample material.

It is known to use other ion sources, such as plasma sources, electron impact ionization sources, etc, capable of producing ion beams with different composition. An example is shown in U.S. Pat. No. 6,236,054, where an electron impact source is described producing ions, said ions accelerated and focused on a sample. Said ion source is sold under the name Gentle Mill™ and described in Application Laboratory Report 68 of South Bay Technology Inc, San Clemente, Calif., and capable of producing a beam with a diameter of 0.75 mm at an ion energy of 300 eV., such as. However, often these sources are less suited for imaging that a LMIS or an electron beam, and therefore these sources are mostly used in dedicated tools for milling, or as an expensive accessory on an imaging tool equipped with a SEM or a FIB column.

There is a need for a cheap, improved method for localized machining or deposition on a charged particle imaging tool equipped with a Scanning Electron Microscope (SEM) column and/or a Focused Ion Beam (FIB) column.

To that end the method according to the invention is characterized in that the charged particle apparatus is equipped with an electrode that is electrically biased with respect to the work piece, said electrode inducing a voltage difference over at least a part of the jet of gas, and a beam of charged particles is directed to the jet of gas between the gas injection system and the work piece or to the gas injection system, as a result of which the beam of charged particles directly or indirectly generates secondary ions that are accelerated to the work piece.

The invention is based on the insight that the beam of charged particles causes ionization of the gas atoms emerging from the gas injection system. These secondary ions are then accelerated to the sample. The secondary ions are generated between the gas injection system and the sample. As the ions are formed between electrode and sample, the energy with which they impinge on the sample is at most the voltage difference between sample and electrode. Therefore it is possible to produce a beam of secondary ions that is proportional to the beam of primary charged particles (electrons or ions), and, assuming a voltage difference U between electrode and sample the energy with which they hit the sample is between zero and U eV.

Preferably the GIS is equipped with a capillary for directing the jet of gas, the capillary acting as the electrode.

Inventors found as a beneficial effect that, when using a beam of electrons as the primary beam of charged particles, and the electrode was the gas injection system, the beam could be caused to hit the capillary of the gas injection system, thereby generating backscattered electrons. This happens for example by the deflection that occurs due to the electric field between sample and electrode: as this field is polarized to accelerate ions to the sample, it is also polarized to attract electrons to the capillary. As backscattered electrons are energetic, the generated backscattered electrons can travel towards the sample before losing all energy (due to the polarization of the electric field, the backscattered electrons are decelerated when travelling in the direction of the sample) and reach the gas jet, where they cause ionization of the gas atoms. The generation of the backscattered electrons can be at the opening of the capillary, at the face of the capillary facing the sample, or even in the capillary by directing the beam of electrons through a slit in the capillary close to the opening.

A preferred method further comprises thinning the sample with a focused ion beam before thinning the sample with the secondary ions.

This causes a rough, fast milling with the focused ion beam, followed by a fine milling to remove the amorphous layer. It can in that respect be comparable to milling and sanding of macroscopic objects.

The gas jet can be a jet comprising a noble gas. Also reactive gases, such as hydrogen for passivation and/or reduction, or oxygen for oxidation, can be guided to the sample.

The gas jet can be a jet comprising a noble gas, but may also comprise reactive gases to include additional chemical reactions by the ion species. The voltage U can be tuned between the milling onset energy and zero, allowing to switch from milling to chemical reactions only. It is foreseen that the function of the primary particle beam in that case is the creation of very low energetic ions and radicals that interact with the surface chemically such as in the case of hydrogen and oxygen.

In an embodiment the GIS is equipped to switch between gasses, thus capable to produce a jet of gas whose composition changes in time.

The energy with which the ions impinge on the sample, causing either milling/sputtering or deposition, is a function of the voltage difference between sample and electrode (capillary) and the position between sample and electrode where the ionization occurs: when said position is chosen close to the sample the energy will be low compared to the situation where the position is close to the capillary. The number of ions generated per second is defined by the primary charged particle beam, when applicable the number of generated energetic electrons and the ionization cross section and possible recombination factors in the gas. The ion current in this way is a parameter independent from the ion energy, unlike a DC gas discharge or an AC plasma discharge It is noted that either the electrode (capillary) or the sample can be connected to earth potential.

To further control the ion energy dependent effects the voltage on the electrode may be modulated.

To localize the gas jet, and thus the ion beam, the distance between GIS and sample is preferably less than 1000 μm, more preferably less than 250 μm, most preferably less than 125 μm.

By scanning the beam of charged particles, the position of the ionization volume can be defined, ranging—in the case where the beam does not hit the capillary—from a small tube (when no scanning occurs) to a plane (when the beam is scanned). This ionization volume then corresponds to a line of ions arriving on the sample to a plane of ions arriving on the sample.

The invention is now elucidated using figures, where identical reference numerals refer to corresponding features. To that end:

FIG. 1 schematically shows a prior art charged particle apparatus.

FIG. 2 schematically shows a detail showing a GIS capillary and a sample

FIG. $3^a$ shows a capillary of a GIS, and

FIG. $3^b$ schematically shows a GIS capillary facing a sample.

Samples, such as semiconductor samples to be imaged in a Transmission Electron Microscope must, after excavating said sample from a wafer, be thinned to form a lamella with a thickness of, for example, 20 nm. This is commonly done by sputtering with ions in a charged particle apparatus equipped with a Scanning Electron Microscope (SEM) column and Focused Ion Beam (FIB) column, further equipped with one or more Gas Injection Systems (GISses).

A problem when milling a lamella to such a thickness is that a large part of the lamella becomes amorphous due to the bombardment with ions, and that ions get implanted in the sample.

FIG. 1 schematically shows a prior art charged particle apparatus.

A charged particle column 110, for example an Scanning Electron Microscope column or a Focused Ion Beam column, comprises a charged particle source 112 for producing a beam of charged particles with a selectable energy of, for example, between 200 eV and 30 keV. The column further comprises one or more charged particle lenses 116, and a condenser lens 108 for focusing the beam on sample 100. A deflector 118 is used for scanning/positioning the beam. The column is mounted on an evacuable sample chamber 102 that can be evacuated by vacuum pumps (not shown). In the sample chamber one or more radiation detectors, such as an Everhart-Thornley detector 130 are used to detect secondary radiation, such as secondary electrons (typically having an energy of less than 50 eV) backscattered electrons (typically having an energy in excess of 50 eV), X-rays, light, etc.. The signal of this detector is connected to signal processor 132 and shown on monitor 134. The sample is positioned by positioning unit 114, typically capable of translating the sample in 3 directions and rotating it in at least 1 direction. A Gas Injection System (GIS) 120 comprises a volume 124 where a gas is stored, a valve 126 to allow gas to flow via capillary 101 to the sample.

Typically the part of the GIS capillary nearest the sample has an outer diameter of between 100 to 1000 μm and an inner diameter of 10 to 50 μm (most typically ~35 μm) in order to get sufficient gas flow, as well as forming an ion source that is sufficiently localized. The capillary is typically moved to a distance of less than 1 mm to the sample, often less than 0.25 mm, thereby providing localized gas supply. By concurrently directing the jet of gas and the focused beam of charged particle to the sample, gas chemistry occurs at the sample leading to etching, deposition (also known as beam induced deposition), etc. This occurs at an even more confined position than the area exposed to the gas, as the focused beam has a diameter of typically between 1 and 5 nm. It is known to deposit lines of, for example, gold, with a width of less than 10 nm by using $Me_2Au(acac)$ as a precursor gas.

It is noted that in this prior art method there is no voltage difference between capillary and sample.

FIG. 2 schematically shows a detail showing a GIS capillary and a sample.

The sample 200 is mounted upright, parallel to the beam of charged particles 206. The metal capillary 201 shows a face 202 facing the sample, and an inner bore 203 from which gas emerges. At the intersect of the beam 206 and the gas jet 207 an ionization volume is formed, from which ions are accelerated towards the sample. A voltage source 208 causes a voltage difference between the capillary and the sample.

It is noted that, by scanning the beam, the ionization volume can be a plane instead of the shown tube.

It is further noted that the beam of charged particles can be made to hit the face of the capillary, thereby forming backscattered electrons that in turn can cause secondary ions. The secondary electrons formed are decelerated and will be directed back to the face of the capillary.

It is also noted that inventors found that, when using a beam of electrons, and reversing the polarity of the voltage source, the beam of electrons could be made to impinge on the sample and an image of the sample could be made. This is especially useful for end-pointing (determining when to stop thinning).

FIG. $3^a$ shows a capillary of a Gas Injection System (GIS).

FIG. $3^a$ shows a tungsten GIS capillary 301 that is cut with an ion beam so as to provide at a distal end a straight face 302, approximately perpendicular to the axis of the capillary. In working this face faces the sample. The axis of the capillary shows an internal bore 303 through which in working the gas is blown out of this capillary. In the wall of the capillary a small rectangle 304 is machined with the ion beam, thereby forming an entrance for an electron beam through the wall of the capillary. By directing the electron beam through this entrance, backscattered electrons and secondary electrons are formed in the bore, and gas passing through the bore is ionized. As these ions still have their initial forward motion due to the gas flow, and are even accelerated out of the capillary by the electric field just outside the capillary, an ion beam emerges from the capillary.

It is noted that surface 305 shown here is only used for holding the capillary during the machining/milling, and is not present in normal use.

FIG. $3^b$ schematically shows the capillary of FIG. $3^a$ facing a sample.

In FIG. $3^b$ a schematic view is given of the GIS capillary 301 shown in FIG. $3^a$ facing a sample 300. The capillary is electrically biased by voltage source 308. Through the slit 304 a beam of electrons is directed along line 306 to the bottom of the central bore 303. This beam of electrons has an energy of, for example, between 0.1 to 30 keV, and causes secondary electrons (normally defined as electrons emerging from a material with an energy of less than 50 eV) and backscattered electrons (normally defined as electrons emerging from a material with an energy in excess of 50 eV) from the bottom of the bore to ionize gas flowing by through the bore. These ions 307, together with gas atoms and/or molecules, emerge from the capillary, due to their initial velocity and the acceleration caused by the electric field between face 302 and the sample. When impinging on the sample, sputtering occurs, the sputter energy approximately equal to the acceleration due to voltage source 308, resulting in very low energy milling.

We claim as follows:

1. A method for removing material from a work piece or depositing material on a work piece using a charged particle apparatus, the charged particle apparatus equipped with:
   a column for producing a beam of charged particles mounted on an evacuable sample chamber,
   a sample position located in the sample chamber, and
   a gas injection system for directing a jet of gas to the sample position,
   the method comprising:
   providing the work piece at the sample position in the sample chamber, the sample chamber being evacuated, and
   directing a jet of gas emerging from a gas injection system to the work piece,
   wherein:
      the gas injection system is equipped with a capillary from which the jet of gas emerges, said capillary being an electrode that is electrically biased with respect to the work piece, said electrode inducing a voltage difference over at least a part of the jet of gas, and a beam of charged particles is directed to the jet of gas between the gas injection system and the work piece or onto a surface of the gas injection system, as a result of which the beam of charged particles directly or indirectly generates secondary ions that are accelerated to the work piece.

2. The method of claim 1 in which the beam of charged particles is a beam of electrons.

3. The method of claim 2 in which the beam of electrons hits the capillary, thereby producing backscattered electrons, the backscattered electrons in turn ionizing gas and thus producing secondary ions.

4. The method of claim 1 in which the accelerated secondary ions thin the work piece and further comprising thinning the work piece with an ion beam produced by an ion beam column prior to thinning the work piece with the secondary ions.

5. The method of claim 1 in which the jet of gas comprises a noble gas.

6. The method of claim 1 in which the jet of gas comprises oxygen or hydrogen.

7. The method of claim 1 in which the gas injection system is equipped to switch between two or more gases, thus capable of producing a jet of gas with a time varying composition.

8. The method of claim 1 in which a voltage difference between the electrode and the work piece is less than 500 eV.

9. The method of claim 1 in which the distance between the gas injection system and the work piece is less than 1 mm.

10. The method of claim 1 in which the beam of charged particles is scanned to define the volume where secondary ions are generated.

11. The method of claim 1 in which the current of the beam of charged particles is modulated.

12. The method of claim 1 in which the work piece is introduced into the sample chamber via an air-lock while the sample chamber is evacuated.

13. The method of claim 1 in which the work piece is introduced into the sample chamber while the sample chamber is vented, and said sample chamber is evacuated afterwards.

14. The method of claim 1 in which the distance between the gas injection system and the work piece is less than 250 µm.

* * * * *